(12) United States Patent
Bischoff et al.

(10) Patent No.: US 10,362,937 B2
(45) Date of Patent: Jul. 30, 2019

(54) CORNEA TRANSPLANTATION

(75) Inventors: Mark Bischoff, Jena (DE); Gregor Stobrawa, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 1432 days.

(21) Appl. No.: 12/597,728

(22) PCT Filed: Apr. 22, 2008

(86) PCT No.: PCT/EP2008/003222
§ 371 (c)(1),
(2), (4) Date: Oct. 26, 2009

(87) PCT Pub. No.: WO2008/131888
PCT Pub. Date: Nov. 6, 2008

(65) Prior Publication Data
US 2010/0087802 A1 Apr. 8, 2010

Related U.S. Application Data

(60) Provisional application No. 60/914,186, filed on Apr. 26, 2007.

(30) Foreign Application Priority Data

Apr. 26, 2007 (DE) .................. 10 2007 019 815

(51) Int. Cl.
| | | |
|---|---|---|
| A61F 2/14 | (2006.01) | |
| A61B 3/107 | (2006.01) | |
| A61F 9/008 | (2006.01) | |

(52) U.S. Cl.
CPC ............. *A61B 3/107* (2013.01); *A61F 2/142* (2013.01); *A61F 2/147* (2013.01);
(Continued)

(58) Field of Classification Search
CPC .................. A61F 9/008–2009/00897
(Continued)

(56) References Cited

U.S. PATENT DOCUMENTS

| | | | |
|---|---|---|---|
| 4,744,362 A | 5/1988 | Gründler | |
| 5,549,632 A * | 8/1996 | Lai ...................... | A61F 9/00825 |
| | | | 606/10 |

(Continued)

FOREIGN PATENT DOCUMENTS

| | | |
|---|---|---|
| DE | 101 24 358 C1 | 10/2002 |
| DE | 10 2004 057 343 A1 | 6/2006 |

(Continued)

OTHER PUBLICATIONS

Bourne et al., "The effects of oversize donor buttons on postoperative intraocular pressure and corneal curvature in aphakic penetrating keratoplasty", Mar. 1, 1982, Ophthalmology, vol. 89, issue 3, pp. 242-246.*

(Continued)

*Primary Examiner* — Lynsey C Eiseman
*Assistant Examiner* — Jonathan Kuo
(74) *Attorney, Agent, or Firm* — Christensen, Fonder, Dardi & Herbert PLLC

(57) ABSTRACT

A planning device generating control data for a treatment apparatus for cornea transplantation using a laser device to separate a corneal volume by at least one cut surface in the cornea and to separate a transplant, from a surrounding transplantation material by at least one cut surface, wherein the planning device includes an interface supplying measurement data relating to parameters of the cornea. A computer defines a corneal cut surface which confines the corneal volume to be removed, and determines a transplant cut surface by using the transplantation material data and depending on the defined corneal cut surface. The transplant (Continued)

cut surface confines the transplant, and the computer generates one control data for each cut surface to control the laser, wherein the respective cut surfaces can be produced by the laser to isolate the corneal volume and the transplant and to make them removable.

17 Claims, 3 Drawing Sheets

(52) U.S. Cl.
CPC ...... *A61F 9/00831* (2013.01); *A61F 9/00827* (2013.01); *A61F 2009/0088* (2013.01); *A61F 2009/00872* (2013.01)

(58) Field of Classification Search
USPC ............................. 606/4–6, 10–12
See application file for complete search history.

(56) References Cited

U.S. PATENT DOCUMENTS

| | | | |
|---|---|---|---|
| 5,647,865 A | 7/1997 | Swinger | |
| 5,984,916 A * | 11/1999 | Lai | B23K 26/0624 606/10 |
| 6,280,470 B1 | 8/2001 | Peyman | |
| 6,299,309 B1 * | 10/2001 | Ruiz | 351/212 |
| 6,805,694 B2 | 10/2004 | Donitzky | |
| 7,351,241 B2 * | 4/2008 | Bendett | A61F 9/00827 606/3 |
| 2002/0077797 A1 * | 6/2002 | Hall | 703/11 |
| 2003/0014042 A1 | 1/2003 | Juhasz et al. | |
| 2003/0199858 A1 * | 10/2003 | Schelonka | 606/5 |
| 2004/0243111 A1 * | 12/2004 | Bendett | A61F 9/00827 606/5 |
| 2005/0117118 A1 * | 6/2005 | Miller et al. | 351/246 |
| 2006/0020259 A1 * | 1/2006 | Baumeister et al. | 606/5 |
| 2006/0155265 A1 | 7/2006 | Juhasz et al. | |
| 2007/0073905 A1 * | 3/2007 | Cynthia et al. | 710/1 |
| 2008/0082086 A1 * | 4/2008 | Kurtz | A61F 2/142 606/4 |
| 2009/0281529 A1 * | 11/2009 | Carriazo | 606/5 |

FOREIGN PATENT DOCUMENTS

| | | |
|---|---|---|
| EP | 1 260 202 A1 | 11/2002 |
| EP | 1 428 470 A2 | 6/2004 |
| EP | 1 719 483 A1 | 11/2006 |
| WO | WO 94/09849 A1 | 5/1994 |
| WO | WO 03/005920 A1 | 1/2003 |

OTHER PUBLICATIONS

Buratto, Lucio, et al., "The Use of the Femtosecond Laser in Penetrating Keratoplasty," *American Journal of Opthalmology*, vol. 143, No. 5, pp. 737-742 (May 2007).

* cited by examiner

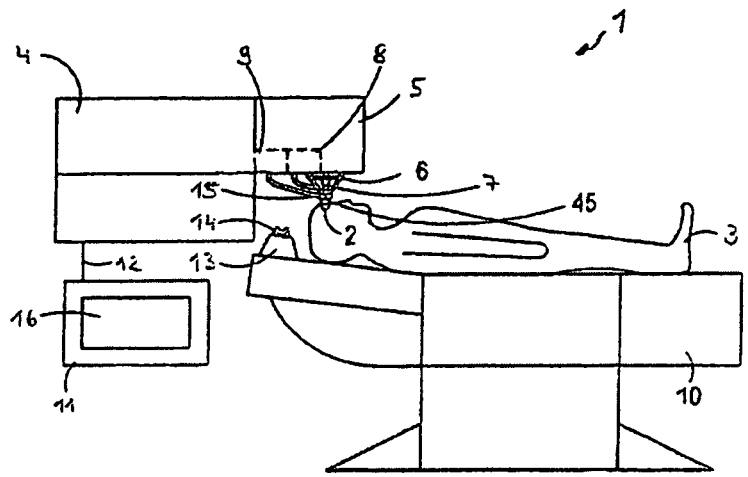
Fig. 1
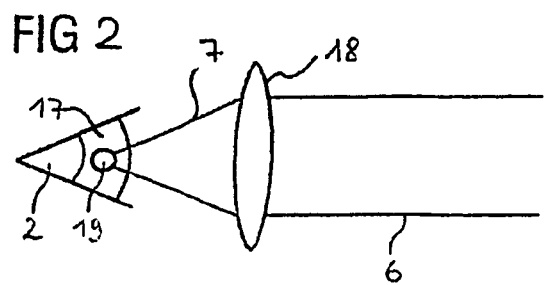
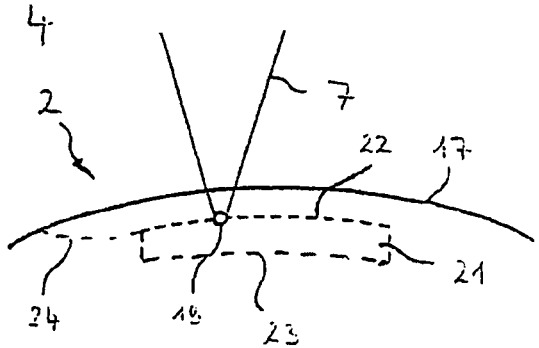

CORNEA TRANSPLANTATION

PRIORITY CLAIM

The present application is a National Phase Entry of PCT Application No. PCT/EP2008/003222, filed Apr. 22, 2008, which claims priority to U.S. Provisional Application No. 60/914,186, filed Apr. 26, 2007, and German Application Number 102007019815.0, filed Apr. 26, 2007, the disclosures of which are hereby incorporated by reference herein in their entirety.

BACKGROUND

The invention relates to a planning device for generating control data for a treatment apparatus for cornea transplantation, said apparatus using a laser device to separate, by at least one cut surface in the cornea, a corneal volume from the surrounding cornea, which corneal volume is to be removed, and to separate, by at least one cut surface in a transplantation material, a transplant from the surrounding transplantation material, which transplant is to be inserted into the cornea.

The invention further relates to a treatment apparatus for cornea transplantation, which comprises a planning device of the aforementioned type.

Further, the invention relates to a method of generating control data for a treatment apparatus for cornea transplantation, which apparatus uses a laser device to separate a corneal volume, which is to be removed, from the surrounding cornea by at least one cut surface in the cornea and to separate a transplant, which is to be inserted into the cornea, from a surrounding transplantation material by at least one cut surface in the transplantation material.

Finally, the invention also relates to a method for cornea transplantation, wherein a treatment apparatus comprising a laser device is used to separate a corneal volume, which is to be removed, from the surrounding cornea by at least one cut surface in the cornea and to separate a transplant, which is to be inserted into the cornea, from a surrounding transplantation material by at least one cut surface in the transplantation material.

It has been known for a long time in ophthalmic surgery to correct changes in the cornea by means of transplantations. The term "transplantation" is understood in this context and also in the following description in the broadest sense, i.e. it comprises an allogenic transplantation, in which the cornea donor and the recipient belong to the same species, i.e. human cornea is transplanted. However, the term also comprises xenogenic transplantation, wherein animal cornea is implanted in the human eye. Further, the term also comprises alloplastic transplantation, wherein artificial material is implanted. The latter is often referred to also as implantation. Further, said term comprises a transplantation, wherein biotechnologically produced cornea (e.g. from stem cells) is used.

It has been known for a long time in the state of the art to carry out transplantations of cornea by cutting a corneal volume to be removed out of the cornea and replacing it with a transplant having, if possible, the same size. In this connection, US 2006/0020259 A1 discloses that the conventional cutting by a knife can be replaced by the use of a treatment apparatus comprising a laser, so that cutting is effected in a contact-free manner by laser radiation.

In addition to healing corneal diseases, transplantations are also known in the state of the art for correction of eyesight defects. In this connection, reference is made especially to WO 03/005920 A1, which teaches to form a pocket in the cornea, into which pocket a transplant is then inserted. The optical effect of the transplant is such that a desired correction of an eyesight defect is achieved thereby. This document also describes it as advantageous to use a laser radiation treatment apparatus to generate the pocket, which is, of course, adapted to the dimensions of the implant.

The already mentioned US 2006/0020259 A1, which intends to replace damaged or diseased cornea by way of transplantation, discloses that a cavity is generated in the cornea by means of laser radiation according to a predetermined cutting pattern. Next, a piece of cornea having, if possible, identical dimensions is cut out of the donor material by laser radiation and is then inserted into the previously generated cavity. The US document describes it as essential for the generated cavity and the cut-out piece to be identical, if possible, and a certain oversize of the transplant is regarded as advantageous for the transplant to be placed in the cavity as securely as possibly. In this case, the US document starts out from a predetermined cutting pattern for the cavity and allows the surgeon to perform minor modifications while cutting the transplant.

Based on a pre-set shape of the cavity, the surgeon can, thus, design the transplant such that its dimensions vary slightly, in order to achieve optimum in-growth of the transplant into the cornea of the recipient.

WO 03/005920 A1, also already mentioned, takes a slightly different approach as compared to the US document, because in the latter, the size of the implant which consists of an artificial material in the WO document, is already fixed and the cavity as well as a required insertion channel are cut to match the given implant.

In both cases, the cut surfaces in the eye are produced by known laser technology using an optical effect of laser radiation in the cornea, for example, by producing an optical breakthrough.

In this case, pulsed laser radiation is usually applied. It is also known to introduce individual pulses, whose energy is below a threshold value for an optical breakthrough, into the tissue or material in a superimposed manner such that a separation of material or tissue is achieved thereby as well.

This concept of producing cuts in the corneal tissue allows a large variety of cuts. The treating surgeon, therefore, theoretically has very great freedom in selecting the cut. However, this does not apply to the approach of WO 03/005920, because the implant to be inserted therein automatically defines the cut surface. According to said reference, the implant is first exactly measured, which then automatically results in the shape of the pocket to be generated for the implant in the cornea, and, thus, inevitably also yields the cut surface in the cornea. US 2006/0020259 A1 does not relate to the shape of the cut at all, but merely refers to a "predetermined cutting pattern". Also, in this reference, the geometry of the cornea of both the recipient and the donor is the same; therefore, the control parameters of the laser device are also identical.

SUMMARY OF THE INVENTION

Thus, both references do not provide a person skilled in the art with any clue as to the cutting pattern to be selected. This is the starting point of the invention. It is an object of the invention to provide assistance allowing exhaustive use of the large variety of possible cut geometries, without undesired influences resulting from predetermined shapes of an implant or predetermined cut surfaces in the recipient's cornea. Also, there is to be greater freedom in selecting the transplantation material.

According to the invention, this object is achieved by a planning device for generating control data for a treatment apparatus for cornea transplantation, which apparatus uses a laser device to separate, by at least one cut surface in the cornea, a corneal volume from the surrounding cornea, which corneal volume is to be removed, and to separate, by at least one cut surface in a transplantation material, a transplant from the surrounding transplantation material, which transplant is to be inserted into the cornea, wherein the planning device comprises an interface for supplying measurement data relating to parameters of the cornea, computing means for defining the corneal cut surface on the basis of the measurement data, which cut surface confines the corneal volume to be removed, wherein said computing means further determine the transplant cut surface, which transplant cut surface depends on the defined corneal cut surface and confines the transplant, and said computing means generate control data sets for the corneal cut surface and the transplant cut surface to control the laser device, wherein the respective cut surfaces can be produced by the laser device when using the control data sets, so as to isolate the corneal volume and the transplant and to make them removable, as well as to make the transplant transplantable.

The object is further achieved by a treatment apparatus for transplantation of cornea of a patient's eye, said apparatus comprising an interface for supplying measurement data relating to parameters of the cornea and for supplying transplantation material data relating to parameters of the transplantation material, the laser device which separates, by at least one cut surface in the cornea, a corneal volume from the surrounding cornea by means of laser radiation according to control data, which corneal volume is to be removed, and separates, by at least one cut surface in the transplantation material, a transplant from a surrounding transplantation material, which transplant is to be inserted into the cornea, and a planning device of the above-described type for generating the control data of the above-described type.

The object is further achieved by a method generating control data for a treatment apparatus for cornea transplantation, said method using a laser device to separate, by at least one cut surface in the cornea, a corneal volume from the surrounding cornea, which corneal volume is to be removed, and to separate, by at least one cut surface in the transplantation material, a transplant from a surrounding transplantation material, which transplant is to be inserted into the cornea, said method comprising the following steps: providing measurement data relating to parameters of the cornea, defining a corneal cut surface using said measurement data, which cut surface confines the corneal volume to be removed, automatically determining a transplant cut surface, said transplant cut surface depending on the defined corneal cut surface and confining the transplant, and generating control data sets for the corneal cut surface and the transplant cut surface in order to control the laser device, so that the respective cut surfaces can be produced by the laser device using the control data sets, in order to isolate the corneal volume and the transplant and to make them removable, as well as to make the transplant transplantable.

Finally, the object is also achieved by a method of cornea transplantation, using a treatment apparatus comprising a laser device to separate, by at least one cut surface in the cornea, a corneal volume from the surrounding cornea, which corneal volume is to be removed, and to separate, by at least one cut surface in the transplantation material, a transplant from a surrounding transplantation material, which transplant is to be inserted into the cornea, said method comprising the following steps: providing measurement data relating to parameters of the cornea, using the measurement data to define a corneal cut surface which confines the corneal volume to be removed, automatically determining a transplant cut surface, said transplant cut surface depending on the defined corneal cut surface and confining the transplant, and generating a control data sets for the corneal cut surface and the transplant cut surface in order to control the laser device, transmitting the control data to the treatment apparatus and producing the respective cut surfaces by using the control data sets to control the laser device, isolating and removing the corneal volume and the transplant and inserting the transplant.

Thus, the invention provides for a planning device and a treatment apparatus, as well as corresponding planning and treatment methods, which assist the generation of control data or the transplantation of cornea such that the corneal cut surface to be formed in the recipient's cornea can be freely selected without having to consider the production of the transplant cut surface by which the transplant is produced from the donor material. The transplant material may comprise both human or animal donor cornea as well as an artificial, in particular a biotechnologically produced material.

According to the invention, the planning device as well as the treatment apparatus equipped therewith and the method for generating the control data or for cornea transplantation automatically generates the control data set matching the freely defined corneal cut surface and causes the appropriate control of the treatment apparatus in order to cut the transplant accordingly. The corneal cut surface can, thus, be selected from a predetermined set as well as be freely defined or composed of predetermined patterns or by modifications of predetermined patterns.

When defining the transplant cut surface, transplantation material data are preferably taken into consideration, because this provides greater freedom in the selection of the transplantation material. For this purpose, the planning device conveniently comprises an interface for supplying transplantation material data relating to parameters of the transplantation material.

The measurement data concerning parameters of the recipient's cornea as well as, where applicable, also the transplantation material data concerning parameters of the transplantation material are conveniently obtained by measuring the recipient's eye or the recipient's cornea or the transplantation material, respectively. In particular, it is possible to determine the geometry of the eye, in particular of the recipient's cornea and, where applicable, of the donor, using a diagnostic device. For this purpose, OCT and ultrasonic systems are suitable, for example, the IOL MASTER or AC MASTER or VISANTE devices of Carl Zeiss Meditec AG, or other systems using optical coherence tomography. The geometries thus determined for the recipient and the donor can relate, for example, to the anterior surface of the cornea and the posterior surface of the cornea, and, where applicable, also to structures within the cornea. If necessary, the position of the eye lens and the parameters of further boundary surfaces or optically active surfaces can be measured and taken into consideration.

The planning device is preferably provided in the form of a planning station, which graphically displays to a user on a screen the acquired measurement data or transplantation material data, either individually or jointly, or even in a superimposed manner. Since the planning task is a spatially complex task in some cases, a 3D screen is provided for easier working.

The computing means conveniently allow a user to input cut geometries, which are subsequently realized. The planning of the cut geometries can then be effected, in a manner similar to a CAD system, in the form of a special linguistic syntax or by a graphic input. It is basically possible that the user may also select, dimension and combine desired shapes from a sort of kit. In example embodiments, software-based control mechanisms are further available in order to check the geometric consistency of the pre-selected cuts, for example, in order to determine and evaluate regions of overlap or contact between cuts.

The computing means allow the user to design the cut individually with utmost liberty in terms of shape. For this purpose, the computing means may comprise a computer.

For further assistance, the computing means or the respective method provide to evaluate the application of symmetries in order to simplify the definition of the corneal cut surface. For example, face and peripheral cuts can be defined in a cylinder-symmetrical manner. Additionally and alternatively, angle-dependent aspect ratios for forming ellipses are possible. For example, the defining means allow the user to program or define peripheral or rim shapes which he knows or assumes to be favorable for the in-growth of the transplant. This includes the possibility for the user to define peripheral cuts allowing him to dispense with sutures for fixing the transplant.

The primary goal of cornea transplantation is usually to replace the diseased or injured corneal tissue, thereby restoring the patient's eyesight. Therefore, in a preferred further embodiment, a refractive correction or the change in refraction by the transplantation is additionally taken into consideration in order to avoid, if possible, any potentially required subsequent refractive corrections. Thus, a further embodiment provides for the computing means to cause a geometrical deviation between the corneal volume and the transplant according to a predetermined change in refraction, when determining the transplant cut surface, in order to achieve not only a replacement of tissue by said transplantation, but also a selective refractive effect. This allows the provision of a transplant such that, after insertion, it has a specific refractive effect together with the remaining refractively effective organs of the recipient's eye, said effect, for example, correcting a previously present eyesight defect. According to this further embodiment, the invention for example, comprises a software tool for evaluating the refractive effect of transplantation as well as means for optimizing at least one refractive cut with respect to the predetermined change in refraction.

The replacement of corneal tissue by way of transplantation quite fundamentally also has an effect on the optical imaging quality, of course, because boundary surfaces which did not exist before are produced in the cornea. The position of the boundary surfaces and, thus, the position of the corneal cut surface is of great importance. Now, in order to allow placing of the cut surface such that the effects on the eye's optical imaging quality after transplantation are minimal, the invention provides a further embodiment of the planning device or of the treatment apparatus, respectively, wherein the computing means compute the transplanted eye's optical imaging quality which is obtained upon carrying out the transplantation, such computing being effected as a function of the corneal cut surface, and display the imaging quality on a display device. For example, a test image or wavefront prognosis data are possible here, whose reproduction is modified according to the imaging quality. Thus, when defining the cut surface, one will automatically see how the selection of the cut surface geometry affects the optical imaging quality.

In order to achieve a maximum degree of automation, it is also possible to input or predetermine in the computing means only the corneal volume which is to be removed during corneal transplantation, and the computing means can then automatically define a setting for the corneal cut surface using predetermined cut geometries or numerical optimization algorithms respectively. This setting is then still optionally modifiable.

Such modification is particularly easy for a user, if a display device for visual representation of the cornea and of the transplantation material is provided with simultaneous representation of the corneal cut surface and of the transplant cut surface.

The measurement data or the transplantation material data, respectively, can be optionally generated by one or more of the following devices: autorefractor, refractometer, keratometer, aberrometer, wavefront measurement device, OCT.

In a further embodiment of the invention, intra-operative monitoring of the cut is provided in the treatment apparatus, so that the progress of the cut is being monitored continuously. In addition, the measurement of the result of surgery can be provided by means of an integrated diagnostic device or a linked diagnostic device, which may be one of the aforementioned measurement devices, for example. The surgical result can be defined in terms of the exact fit of the inserted transplant, the sizes of cavities or the absence of cavities, respectively, warping of the cornea or of the inserted transplant, the number and size of epithelial cells carried into the stroma, or the absence of such epithelial cells, respectively, soiling of the cornea, for example, by fibers etc.

BRIEF DESCRIPTION OF THE DRAWINGS

It will be appreciated that the aforementioned features and those yet to be explained below can be employed not only in the indicated combinations, but also in other combinations or alone, without departing from the scope of the present invention.

The invention will be explained in more detail below, by way of example and with reference to the drawing, wherein:

FIG. 1 is a schematic representation of a treatment apparatus comprising a planning device for carrying out a cornea transplantation;

FIG. 2 is a schematic representation of the effect of laser radiation used in the treatment apparatus of FIG. 1;

FIG. 4 is a schematic sectional view of the cornea, illustrating the removal of the corneal volume in connection with the cornea transplantation;

DETAILED DESCRIPTION

Figure 3:
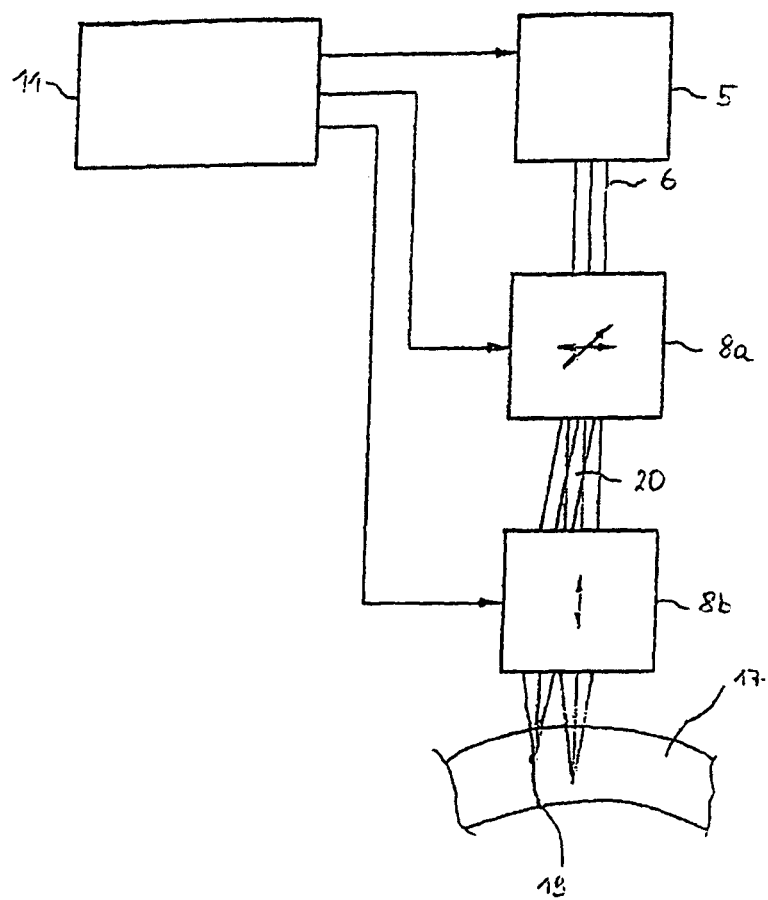
FIG. 3 is a further schematic representation of the treatment apparatus of FIG. 1 with respect to the introduction of laser radiation.

A treatment apparatus for cornea transplantation is shown in FIG. 1 and bears the general reference numeral 1. Using the treatment apparatus 1, a cornea transplantation is carried out on an eye 2 of a patient 3. For this purpose, the treatment apparatus 1 comprises a laser device 4, which emits a laser beam 6 from a laser source 5, said laser beam 6 being directed into the eye 2 or the cornea, respectively, as a focused beam 7. The laser beam 6 is for example a pulsed laser beam having a wavelength of between 400 nanometers and 10 micrometers. Further, the pulse duration of the laser beam 6 is in the range between 1 femtosecond and 10 picoseconds, allowing pulse repetition frequencies of 1 to 1000 kilohertz and pulse energies of between 0.01 microjoules and 10 microjoules. Thereby, the treatment apparatus 1 produces a cut surface in the cornea of the eye 2 by deflecting the pulsed laser radiation. Further, a scanner 8 as well as a radiation-intensity modulator 9 is provided in the laser device 4 or its laser source 5, respectively.

The patient 3 is lying on a table 10, which is shiftable in three spatial directions in order to align the eye 2 with the incidence of the laser beam 6. In an example construction, the table 10 is shiftable by a motor drive.

Control may be effected, in particular, by a control device 11 which generally controls the operation of the treatment apparatus 1 and is connected to the treatment apparatus via suitable data links, for example connecting lines 12, for this purpose. This communication may, of course, be effected also via other paths, for example by light guides or by radio. The control device 11 performs the corresponding settings, time control of the treatment apparatus 1, in particular of the laser device 4, and thus performs corresponding functions of the treatment apparatus 1.

As shown in FIG. 1, not only the table 10, on which the patient 3 is lying, is provided in connection with the treatment apparatus 1, but also a fixture 13, which holds donor cornea (not shown in FIG. 1), for example, by the use of a mount 14. The fixture 13 is provided such that it matches the shape of the present donor cornea. For example, in the case of a donor's eye, the mount 14 shown as an example in FIG. 1 can be used. In the case of already removed cornea or in the case of synthetically produced cornea or cornea from animal tissue, respectively, the fixture can also be designed differently, for example, without the mount 14. The mount 14 generally has a design matching the transplantation material from which the transplant is cut out.

The treatment apparatus 1 further comprises a fixing device 15, which positionally fixes the cornea of the eye 2 with respect to the laser device 4. This fixing device 15 may comprise a known contact glass 45, which is placed in contact with the cornea by a vacuum and which imparts a desired geometrical shape to the cornea. Such contact glasses are known to the person skilled in the art from the state of the art, for example from DE 102005040338 A1. The disclosure of this document is fully incorporated herein by reference as far as the description of a construction of the contact glass 45 possible for the treatment apparatus 1 is concerned.

The control device 11 of the treatment apparatus 1 further comprises a planning device 16, which will be explained in more detail below.

FIG. 2 schematically shows the effect of the incident laser beam 6. The laser beam 6 is focused and is incident as the focused laser beam 7 in the cornea 17 of the eye 2. Schematically shown optics 18 are provided for focusing. They effect a focus in the cornea 17, in which focus the laser radiation energy density is so high that, in combination with the pulse duration of the pulsed laser radiation 6, a non-linear effect appears in the cornea 17. For example, each pulse of the pulsed laser radiation 6 in the focus 19 may produce an optical breakthrough in the cornea 17, which in turn initiates a plasma bubble indicated only schematically in FIG. 2. When the plasma bubble forms, the tissue layer separation comprises an area larger than the focus 19, although the conditions for producing the optical breakthrough are achieved only in the focus 19. In order for an optical breakthrough to be produced by each laser pulse, the energy density, i.e. the fluence of the laser radiation, must be above a certain pulse duration-dependent threshold value. This connection is known to the person skilled in the art, for example, from DE 69500997 T2. Alternatively, a tissue-separating effect can also be achieved by pulsed laser radiation in that several laser radiation pulses are emitted into a region where the focus spots overlap. In this case, several laser radiation pulses cooperate to achieve a tissue-separating effect.

However, the type of tissue separation used by the treatment apparatus is not really relevant to the following description; it is only essential that a cut surface is generated in the cornea 17 of the eye 2.

Now, in order to perform a transplantation of cornea, a corneal volume is removed from a region within the cornea 17 by means of the laser radiation 6, separating tissue layers therein which isolate the corneal volume and enable removal of the latter then. For isolation of the corneal volume to be removed, the position of the focus 17 of the focused laser radiation 7 in the cornea 17 is shifted for example, in cases where pulsed laser radiation is introduced. This is schematically shown in FIG. 3.

FIG. 3 shows the elements of the treatment apparatus 1 only insofar as they are required in order to understand how the cut surfaces are produced. As already mentioned, the laser beam 6 is bundled into a focus 19 in the cornea 17, and the position of the focus 19 in the cornea is shifted such that focused energy from laser radiation pulses is introduced into the tissue of the cornea 17 at different locations so as to produce cut surfaces. The laser radiation 6 may be provided by the laser source 5 as pulsed radiation. The scanner 8 has a two-part design in the construction of FIG. 3 and consists of an xy-scanner 8a, which is realized, in one variant, by two galvanometer mirrors with substantially orthogonal deflection. The scanner 8a two-dimensionally deflects the laser beam 6 coming from the laser source 5, so that a deflected laser beam 20 is present behind the scanner 8. Thus, the scanner 8a causes shifting of the position of the focus 19 substantially perpendicular to the main direction of incidence of the laser beam 6 in the cornea 17. For shifting of the depth position, a z-scanner 8b is provided in the scanner 8 in addition to the xy-scanner 8a, for example, in the form of an adjustable telescope. The z-scanner 8b provides for changes of the z-position of the focus 19, i.e. of its position along the optical axis of incidence. The z-scanner 8b may be arranged preceding or following the xy-scanner 8a.

It is not essential for the functional principle of the treatment apparatus 1 how the individual coordinates are assigned to the spatial directions nor that deflection by the scanner 8a is effected along mutually orthogonal axes. On the contrary, any scanner may be used which can shift the focus 19 in a plane in which the axis of incidence of the optical radiation is not located.

Of course, it is also possible to use any non-Cartesian coordinate systems whatsoever for deflection or control of the position of the focus 19. Examples include spherical coordinates or cylindrical coordinates.

The position of the focus 19 is controlled by the scanners 8a, 8b under control of the control device 11, which performs suitable settings of the laser source 5, of the modulator 9 (not shown in FIG. 3) as well as the scanner 8. The control device 11 ensures suitable operation of the laser source 5 as well as the three-dimensional focus shift described here as an example, thus finally producing a cut surface which isolates a defined corneal volume that is to be removed for transplantation.

The control device 11 works according to predetermined control data, which are specified, for example, to the laser device 4 described here merely as an example, as target points for focus shifting. The control data are usually compiled in a control data set, which provides geometrical parameters for the cut surface to be formed, e.g. the coordinates of the target points as a pattern. In this embodiment, the control data set then also includes concrete set values for the focus position shifting mechanism, e.g. for the scanner 8.

FIG. 4 shows an example of how to produce the cut surface using the treatment apparatus 1. A corneal volume 21 is isolated in the cornea 17 by shifting the focus 19, into which the focused beam 7 is bundled. For this purpose, cut surfaces are formed, which are provided here, by way of example, as an interior flap cut surface 22 as well as a posterior lenticle cut surface 23. These terms are to be understood here merely as examples and are intended to refer to the conventional LASIK or FLEX methods, for which the treatment apparatus 1 is known, as already described. It is only essential here that the cut surfaces 22 and 23 as well as peripheral cuts, which are not referred to in detail, isolate the corneal volume 21. Further, a corneal lamella anteriorly limiting the corneal volume 21 can be folded aside due to a peripheral cut 24 so as to allow removal of the corneal volume 21. The type of isolation of the corneal volume 21 and its removal is not vital for the present invention and other embodiments are also possible.

Figure 5A:
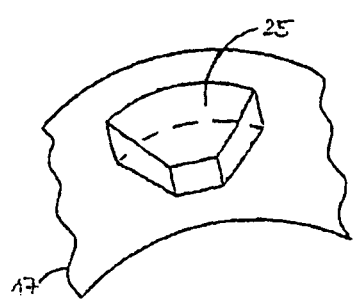
FIG. 5a is a perspective view of a cavity produced in the recipient's cornea.
Figure 5B:
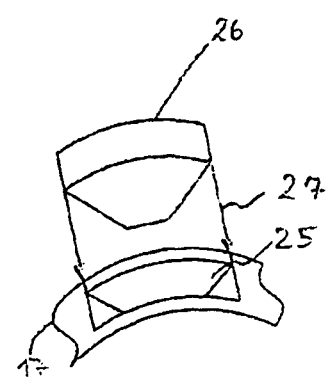
FIG. 5b is a perspective view of the transplant prior to insertion into the recipient's cornea.

FIG. 5a schematically shows the state after removal of the corneal volume. Thus, a chamber 25 has been formed in the cornea 17, said chamber serving as a cavity which receives the transplant. The transplant is cut out from a transplantation material, also using the treatment apparatus 1, preferably using precisely the same effects and mechanisms which were employed in order to produce the chamber 25. The transplant 26 thus produced is then inserted, as FIG. 5b shows, into the chamber 25, which process is illustrated by arrows 27 in FIG. 5b.

Figure 6:
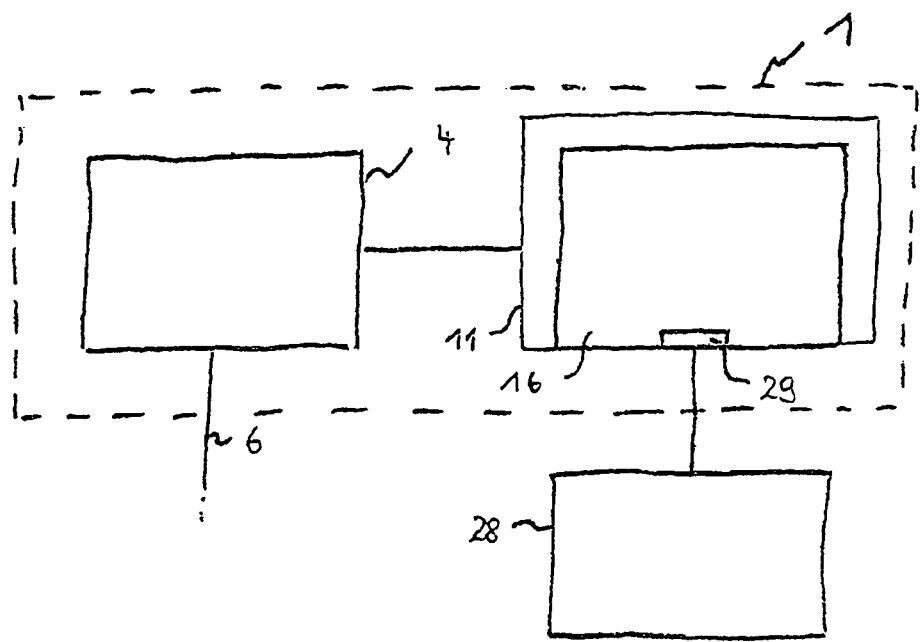
FIG. 6 is a schematic view of the construction of the treatment apparatus of FIG. 1 with particular reference to the planning device present.

FIG. 6 schematically shows the treatment apparatus 1, by reference to which the importance of the planning device 16 shall be explained in more detail. In this variant, the treatment apparatus 1 comprises at least two devices or modules. The laser device 4 already described emits the laser beam 6 onto the eye 2. As already described, operation of the laser device 4 is effected fully automatically by the control device 11, i.e. the laser device 4 starts generating and deflecting the laser beam 6 in response to a corresponding start signal and, thus, generates cut surfaces, which are structured as described, in order to remove the corneal volume 21 or to generate the transplant 26 from the transplantation material. The laser device 4 receives the control signals required for operation from the control device 11, to which corresponding control data have been provided before. This is effected by the planning device 16, which is shown in FIG. 6 merely by way of example, as part of the control device 11. Of course, the planning device 16 may also be provided separately and may communicate with the control device 11 either in a wire-bound or wireless manner. It is then only essential to provide a corresponding data transmission channel between the planning device 16 and the control device 11.

The planning device 16 generates a control data set which is provided to the control device 11 to carry out the transplantation. In doing so, the planning device uses measurement data relating to the cornea of the eye as well as transplantation material data relating to the transplantation material from which the transplant 26 is to be cut out. In the present embodiment, these data come from a measurement device 28, which has previously measured the eye 2 of the patient 2. A similar measurement device 28 may, of course, be provided for the transplantation material as well. Of course, the measurement device 28 may have any design whatsoever and may transmit the corresponding data to the interface 29 of the planning device 16.

The data relating to the transplantation material may also come from other sources and need not be generated before directly by a measurement.

Now, the planning device assists the user of the treatment apparatus 1 in defining the cut surface for isolation of the corneal volume 21. This may even include a fully automatic definition of the cut surfaces, which may be effected, for example, by the planning device 16 recognizing the corneal volume 21 to be removed from the measurement data, defining the boundary surfaces of said corneal volume 21 as cut surfaces, and generating therefrom suitable control data for the control device 11. At the other end of the degree of automation, the planning device 16 may provide input means by which a user inputs the cut surfaces in the form of geometrical parameters, etc. Intermediate degrees provide suggestions for the cut surfaces, which the planning device 16 generates automatically and which can then be modified by an operator. Basically, all the concepts already explained in the above, more generic part of the specification can be applied here in the planning device 16.

After defining the cut surfaces for the corneal volume 21, the planning device 16 uses a computing unit (e.g. a computer) provided therein, on the one hand, to generate the control data for producing the chamber 25, and, on the other hand, also to compute the cut surfaces for cutting the transplant 26. In doing so, it preferably takes the transplantation material data into consideration. The control data for the transplantation cut are generated automatically.

Further, a desired correction of an eyesight defect can be defined, which the computing unit then converts into a geometrical deviation between the chamber 25 and the transplant 26 in order to modify the corneal refraction accordingly.

The planning device 16 serves to define cut surfaces for cornea transplantation. For this purpose, it is supplied with data relating to the eye as well as data relating to the transplantation material and generates, preferably depending on previously input parameters, the control data for producing the cut surface on the eye, and automatically generates matching control data for cutting the transplant. In doing so, it is essential for the planning device that, first, the cut surface is defined for isolation of the corneal volume and then, based on such corneal cut surface, the corresponding transplant cut surfaces are determined. Such determination is preferably effected fully automatically.

In this case, parameters can be taken into consideration which result from the geometry and structure of the transplantation material. Additional parameters, which may be included in automatically determining the transplant cut surfaces, comprise the already mentioned correction of eyesight defects. In this case, the transplant cut surface is formed to deviate from the corneal cut surface such that the transplant, once inserted, has a certain refractive effect together with the remaining refractive elements of the recipient's eye to modify the initial pre-transplantation refraction.

In a specific embodiment, the planning device 16 uses the determination of the geometry of the recipient's eye, in particular of the cornea of the recipient's eye, and preferably, as already explained, also the geometry of the transplantation material, e.g. of donor cornea. The measurement devices or diagnostic devices already mentioned in the generic part of the specification are suitable for this purpose and can communicate with the planning device 16 via a corresponding data communication channel, as already described above.

The detectable geometries of the recipient's eye or of the transplantation material comprise, for example, the shape of the anterior corneal surface and of the posterior corneal surface as well as structures within the recipient's cornea, and, where applicable, also the position of the eye lens and of further boundary surface parameters. In a preferred embodiment, individual or several of these geometries or geometrical parameters, respectively, are graphically displayed for the user on a screen, in which case a superimposed graphic display is also possible.

Planning of the cut geometries can be assisted by the planning device 16 in a manner similar to a CAD system in the form of a special linguistic syntax or by means of a graphic input. Conveniently, it is also possible to provide the planning device with a memory, which stores possible geometries for the corneal cut surface, for example in the manner of a kit. The user can then select, dimension and combine the desired shapes. Moreover, the planning device 16 may comprise further special control mechanisms which examine and evaluate the overlap or the contact of cut surfaces in determining the corneal cut surface and, where applicable, effect a corresponding display or reject a cut input by the user.

In this manner, an individual design of the cut can be facilitated for the user, with almost complete freedom in terms of shapes. In order to make it easier to define a certain shape, it is preferred for the planning device to utilize symmetries when producing cut surfaces. For example, face and peripheral cuts may preferably be designed to have cylindrical symmetry. In addition, angle-dependent aspect ratios for generating elliptical shapes are possible. Moreover, the planning device may allow for the peripheral surfaces of the corneal volume to he defined such that sutures for fixing the transplants become unnecessary.

Of course, the planning device as well as the treatment apparatus may be combined with each other and with further devices as desired. In particular, a data network of diagnostic devices and treatment devices may be used.

However, an independent planning device 16 has advantages in terms of sterility, because the planning device 16 can then be arranged outside the sterile operating area, which facilitates intensive planning work. Of course, if priority is given to very rapid planning, the planning device may also be arranged within the sterile operating area.

The cut surfaces for both the cornea and the transplant are usually two-dimensionally curved cuts. Therefore, the planning device provides corresponding input possibilities and, in particular a graphic input of the corneal cut surfaces, a graphic representation of the cut resulting there from, as well as means for computing and optimizing a refractive effect.

It should also be noted that the treatment apparatus 1 or the planning device 16, of course, also specifically executes the method generally explained above.

A further embodiment of the planning device is in the form of a computer program or of a corresponding data carrier comprising a computer program, which implements the planning device on one or more interconnected computers, so that the input of the measurement data or the transplantation material data into the computer is effected by a suitable data transmission means, and the control data are transmitted from this computer to the control device 11, for which purpose data transmission means, again known to the person skilled in the art, are suitable.

The invention claimed is:

1. A method for generating control data for a laser treatment apparatus for transplanting corneal material from a donor cornea of an eye of a donor to a patient cornea of an eye of a patient, and for correcting refractive deficiencies of the patient cornea, said method comprising:

receiving from a measurement device, measurement data relating to parameters of an eye of a patient at an interface device to a computing unit;

transmitting the measurement data from the interface device to the computing unit communicatively coupled to the interface device, the transmitted measurement data including data defining a geometry of the eye of the patient, the geometry including a pre-transplantation shape of a front surface of the patient cornea, based on the measurement data received from the computer interface, using the computer to automatically determine:

a previously-present refractive deficiency of the eye of the patient, and a change of the pre-transplantation shape of the front surface of the patient cornea, the change being required to correct the previously-present refractive deficiency of the eye, boundary surfaces in the patient cornea, the boundary surfaces in the patient cornea defining a patient corneal volume to be removed from the patient cornea, the boundary surfaces in the patient cornea including an anterior cut surface lying beneath a front surface of the patient cornea, and a posterior cut surface lying beneath the front surface of the patient cornea, the boundary surfaces in the patient cornea defined such that the patient corneal volume is initially surrounded by corneal tissue of the patient cornea and is beneath the front surface of the patient cornea, boundary surfaces in the donor cornea, the boundary surfaces in the donor cornea defining a transplant corneal volume to be removed from the donor cornea, the boundary surfaces in the donor cornea including an anterior boundary surface lying beneath a front surface of the donor cornea, and a posterior cut surface lying beneath the front surface of the donor cornea, the boundary surfaces in the donor cornea defined such that the transplant corneal volume is initially surrounded by corneal tissue of the donor cornea and is beneath the front surface of the donor cornea, and wherein a size of the transplant corneal volume differs from a size of the patient corneal volume;

generating control data sets for controlling a laser device of a treatment apparatus, including generating a transplant control data set, and generating a patient control data set, and transmitting the control data sets to the laser treatment apparatus for generation of the cut surfaces in the donor cornea and the patient cornea;

wherein automatically determining the boundary surfaces defining the patient corneal volume and the transplant corneal volume includes defining a deviation between the size of the patient corneal volume and the size of the transplant corneal volume, the deviation causing a change in the geometry of the eye of the patient, including a change in the pre-transplantation shape of the front surface of the patient cornea once the transplant corneal volume replaces the patient corneal volume, to correct the previously-present refractive deficiency.

2. The method as claimed in claim 1, further comprising offering a user of the laser treatment apparatus a selection of pre-stored boundary surface geometries which define the transplant corneal volume.

3. The method as claimed in claim 2, further comprising modifying the pre-stored boundary surface geometries and storing modified boundary surface geometries.

4. The method as claimed in claim 1, further comprising computing an expected optical imaging quality that the eye of the patient will have after carrying out the transplantation, the expected optical imaging quality being a function of the defined boundary surfaces, and displaying a representation of the expected optical imaging quality on a display device.

5. The method as claimed in claim 1, including defining the transplant corneal volume to be removed during transplantation when defining the boundary surfaces of the donor cornea.

6. The method as claimed in claim 1, wherein the cornea and the transplantation material are represented on a display simultaneously with the boundary surfaces in the patient cornea and the donor cornea.

7. The method as claimed in claim 1, further comprising generating the measurement data from a measurement of the eye and/or the transplantation material data using the measurement device.

8. The method as claimed in claim 7, wherein the measurement device is selected from a group consisting of the following devices: an autorefractor, a refractometer, a keratometer, an aberrometer, a wavefront measurement device, an OCT and a combination of the foregoing.

9. A non-transitory, computer-readable medium comprising program code which, when being executed on a computer, carries out the method as claimed in claim 1.

10. A method for transplanting corneal material from a donor cornea of an eye of a donor to a patient cornea of an eye of a patient, and for correcting refractive deficiencies of the patient cornea, comprising:
using a measurement device to measure parameters of the eye of the patient and obtain measurement data relating to parameters of the cornea, including measurement data defining a geometry of the eye of the patient, the geometry including a pre-transplantation shape of a front surface of the patient cornea,
transmitting the measurement data to a computer interface of a planning device;
based on the measurement data received from the computer interface of the planning device, using a computer of the planning device to automatically determine:
a previously-present refractive deficiency of the eye, and a change of the pre-transplantation shape of the front surface of the patient cornea, the change being required to correct the previously-present refractive deficiency of the eye,
boundary surfaces in the patient cornea, the boundary surfaces in the patient cornea defining a patient corneal volume to be removed from the patient cornea, the boundary surfaces in the patient cornea including an anterior cut surface lying beneath the front surface of the patient cornea, and a posterior cut surface lying beneath the front surface of the patient cornea, the boundary surfaces in the patient cornea defined such that the patient corneal volume is initially surrounded by corneal tissue of the patient cornea and is beneath the front surface of the patient cornea,
boundary surfaces in the donor cornea, the boundary surfaces in the donor cornea defining a transplant corneal volume to be removed from the donor cornea, the boundary surfaces in the donor cornea including an anterior boundary surface lying beneath a front surface of the donor cornea, and a posterior cut surface lying beneath the front surface of the donor cornea, the boundary surfaces in the donor cornea defined such that the transplant corneal volume is initially surrounded by corneal tissue of the donor cornea and is beneath the front surface of the donor cornea, and wherein a size of the transplant corneal volume differs from a size of the patient corneal volume;
generating control data sets for controlling a laser device of a treatment apparatus, including generating a transplant control data set, and generating a patient control data set,
transmitting the control data sets to the treatment apparatus,
generating the boundary surfaces in the donor cornea;
separating the transplant donor volume from the donor cornea;
generating the boundary surfaces in the patient cornea by controlling the laser device using the patient control data set, thereby isolating the patient corneal volume,
removing the patient corneal volume, and
inserting the transplant corneal volume, which has a different size as compared to the patient corneal volume, into the eye of the patient;
wherein automatically determining the boundary surfaces defining the patient corneal volume and the transplant corneal volume includes defining a deviation between the size of the patient corneal volume and the size of the transplant corneal volume, the deviation causing a change in the geometry of the eye of the patient, including a change in the pre-transplantation shape of the front surface of the patient cornea once the transplant corneal volume replaces the patient corneal volume, to correct the previously-present refractive deficiency.

11. The method as claimed in claim 10, further comprising offering a user of the laser treatment apparatus a selection of pre-stored boundary surface geometries which define the transplant corneal volume.

12. The method as claimed in claim 11, further comprising modifying the pre-stored boundary surface geometries and storing modified boundary surface geometries.

13. The method as claimed in claim 10, further comprising computing an expected optical imaging quality that the eye of the patient will have after carrying out the transplantation, the expected optical imaging quality being a function of the defined boundary surfaces, and displaying a representation of the expected optical imaging quality on a display device.

14. The method as claimed in claim 10, including defining the transplant corneal volume to be removed during transplantation when defining the boundary surfaces of the donor cornea.

15. The method as claimed in claim 10, wherein the cornea and the transplantation material are represented on a display simultaneously with the boundary surfaces in the patient cornea and the donor cornea.

16. The method as claimed in claim 10, further comprising generating the measurement data from a measurement of the eye and/or the transplantation material data using the measurement device.

17. The method as claimed in claim 16, wherein the measurement device is selected from a group consisting of the following devices: an autorefractor, a refractometer, a keratometer, an aberrometer, a wavefront measurement device, an OCT and a combination of the foregoing.

\* \* \* \* \*

UNITED STATES PATENT AND TRADEMARK OFFICE
CERTIFICATE OF CORRECTION

| | |
|---|---|
| PATENT NO. | : 10,362,937 B2 |
| APPLICATION NO. | : 12/597728 |
| DATED | : July 30, 2019 |
| INVENTOR(S) | : Mark Bischoff and Gregor Stobrawa |

Page 1 of 1

It is certified that error appears in the above-identified patent and that said Letters Patent is hereby corrected as shown below:

On the Title Page

Page 2, Item (56), References Cited, U.S. PATENT DOCUMENTS, add -- 5,677,750 A 10/1997 Qi --, therefore.

In the Specification

In Column 11, Line 45, delete "he" and insert -- be --, therefore.

Signed and Sealed this
Third Day of March, 2020

Andrei Iancu
*Director of the United States Patent and Trademark Office*